United States Patent [19]
Lambert et al.

[11] Patent Number: 5,606,973
[45] Date of Patent: Mar. 4, 1997

[54] LIQUID CORE MICRODROPLETS FOR ULTRASOUND IMAGING

[75] Inventors: Karel J. Lambert, San Diego; Edward G. Jablonski, Escondido, both of Calif.

[73] Assignee: Molecular biosystems, Inc., San Diego, Calif.

[21] Appl. No.: 483,127

[22] Filed: Jun. 7, 1995

[51] Int. Cl.⁶ ........................................................ A61B 8/00
[52] U.S. Cl. ........................................ 128/662.02; 424/9.5
[58] Field of Search ........................ 128/662.02, 660.01; 424/9.52, 9.5, 673, 9.43; 264/4, 4.1, 4.3

[56] References Cited

U.S. PATENT DOCUMENTS

| | | | |
|---|---|---|---|
| 5,409,688 | 4/1995 | Quay | 424/9.52 |
| 5,425,366 | 6/1995 | Reinhardt et al. | 128/662.02 |
| 5,439,686 | 8/1995 | Desai et al. | |
| 5,469,854 | 11/1995 | Unger et al. | 128/662.02 |

*Primary Examiner*—George Manuel
*Attorney, Agent, or Firm*—Morrison & Foerster

[57] ABSTRACT

Ultrasonic imaging agents comprising an aqueous suspension of negatively buoyant aspherical microdroplets composed of a biocompatible liquid core encapsulated by a shell of amphiphilic biocompatible material are prepared by milling a mixture of a solution of the shell material and vaporized liquid and cooling the milled mixture to below the boiling point of the liquid.

19 Claims, No Drawings

LIQUID CORE MICRODROPLETS FOR ULTRASOUND IMAGING

DESCRIPTION

1. Technical Field

This invention is in the field of ultrasound contrast agents. More particularly, it concerns an ultrasound imaging agent comprising a biocompatible liquid core encapsulated by a biocompatible shell-forming material.

2. Background

Diagnostic ultrasound imaging is based on the principle that waves of sound energy can be focused upon an area of interest and reflected in such a way as to produce an image thereof. The ultrasonic scanner is placed on a body surface overlying the area to be imaged, and sound waves are directed toward that area. The scanner detects reflected sound waves and translates the data into a video image. When ultrasonic energy is transmitted through a substance, the amount of energy reflected depends upon the velocity of the transmission and the acoustic properties of the substance. Changes in the substance's acoustic properties (i.e., variations in acoustic impedance) are most prominent at the interface of different acoustic densities, such as liquid-solid or liquid-gas. Consequently, when ultrasonic energy is directed through tissue, organ structures generate sound reflection signals for detection by the ultrasonic scanner. These signals can be intensified by the proper use of a contrast agent.

Orphir and Parker, Ultrasound in Medicine and Biology 15(4):319-333 (1989) describe various types of gas-containing ultrasound contrast agents. Ultrasound contrast agents are well-known in the art and generally consist of air or other microbubbles of gaseous compounds stabilized in liquid emulsions (e.g., PCT/US92/09250), encapsulated in a solid shell (e.g., U.S. Pat. Nos. 4,572,203 and 4,844,882), or embedded in a solid matrix (e.g., EP 0 035 467 and 0 122 624). Other patent literature describes other types of contrast agents such as liquid-liquid emulsions in which the dispersed liquid has a boiling point below physiological temperature (e.g., PCT WO 94/16739). When the emulsion is administered, the dispersed liquid boils.

Gas-core agents have low density and maximize echogenicity due to the relatively large density differential between the gas environment and the surrounding solid or liquid environment. These agents are effective backscatterers of ultrasound in vivo, but the duration of the effect is limited by the eventual solubilization of the air core into the surrounding serum. The evolution of gaseous ultrasound agents containing relatively insoluble gases increases the in vivo half-life merely to the order of minutes.

In some cases, it would be desirable to have an ultrasound contrast effect of even greater duration on the order of one half to two hours. In an effort to create such an agent it is envisioned that longevity may be increased at the expense of diminished echogenicity. This would permit dosing the patient prior to the to the examination, or allow time for interrogation of the entire region or organ of interest. More importantly, it would allow for improved doppler imaging.

DISCLOSURE OF THE INVENTION

One aspect of the invention is a composition for use as an ultrasonic imaging agent comprising a suspension of microdroplets, said microdroplets comprising at least one biocompatible liquid as a core encapsulated by a biocompatible shell-forming material.

An other aspect of the invention is a method of enhancing the contrast of tissue and/or organs of a patient in an ultrasonic image thereof comprising:

(a) injecting the above-described composition into the patient;

(b) applying ultrasonic energy to said tissue and/or organs;

(c) detecting ultrasonic energy that is reflected from the tissues and/or organs; and (d) translating the reflected energy into an image.

MODES FOR CARRYING OUT THE INVENTION

The microdroplets of the invention have an aspherical shell which is an amphiphilic biocompatible material formed by mechanical cavitation, such as occurs in a colloid mill. Amphiphilic materials have both hydrophilic and hydrophobic groups. Different classes of materials that would be suitable for forming microsphere shells include, but are not limited to lipids, proteins (both naturally occurring and synthetic amino acid polymers), synthetic organic polymers, and mixtures or copolymers thereof.

Lipid shells may be formed from either naturally occurring or synthetic lipids, for example, phospholipids, such as phosphoglycerides, phosphatidic acid, phosphatidylcholine, phosphatidyl serine, phosphatidylethanolamine, phosphatidyl inositol, phosphatidyl glycerol, diphosphatidyl-glycerol (cardiolipin); glycolipids, such as cerebrosides, galactocerebrosides, gluco-cerebrosides, sphingomyelin, sphingolipids, derivatized with mono-, di-, and trihexosides, sulfatides, glycosphingolipid, and lysophosphatidylcholine; unsaturated fatty acids, such as palmitoleic acid, oleic acid, vaccenic acid, linoleic acid, α-linolenic acid, and arachadonic acid; saturated fatty acids, such as myristic acid, palmitic acid, stearic acid, arachidic acid, behenic acid, lignoceric acid, and cerotic acid; mono-, di-, and triglycerides; and steroids, such as cholesterol, cholesterol esters, cholestanol, ergosterol, coprostanol, squalene, and lanosterol.

Lipid shells may also optionally incorporate proteins, amino acid polymers, carbohydrates or other substances useful for altering the rigidity, elasticity, biodegradability, and/or biodistribution characteristics of the shell. Incorporation of sterols is particularly useful in increasing the rigidity of the shell. The rigidity of the shell can also be enhanced by cross-linking, for example, by irradiation.

Protein shell material includes both naturally occurring filmogenic proteins and synthetic amino acid polymers which herein are both generally referred to as being in the class of shell materials described as "proteins." The term "filmogenic" intends a soluble protein that is able to form a shell or film about a biocompatible liquid core when the protein is insolubilized by cavitation. Suitable proteins include naturally occurring proteins such as albumin, gamma-globulin (human), apo-transferrin (human), β-lactoglobulin, urease and lysozyme, as well as synthetic amino acid polymers. Particularly well-suited for the present invention is albumin, and more particularly, human albumin.

Synthetic organic polymers are also suitable for forming the microdroplet shells. These polymers can consist of a single repeating unit or different repeating units which form a random, alternating or block-type copolymer. See, for instance, PCT Application No. WO 95/06518 the disclosure of which is incorporated herein by reference. These organic polymers include cross-linked polyelectrolytes such as phosphazenes, imino-substituted polyphosphazenes, polyacrylic acids, polymethacrylic acids, polyvinyl acetates, polyvinyl amines, polyvinyl pyridine, polyvinyl imidazole, and ionic salts thereof. Cross-linking of these polyelectrolytes is accomplished by reaction of multivalent ions of the opposite charge. Further stabilization can be accomplished by adding a polymer of the same charge as the polyelectrolyte. See U.S. Pat. No. 5,149,543 which is incorporated herein by reference.

Additional synthetic organic monomeric repeating units which can be used to form polymers suitable for shell materials within the present invention are hydroxyacids, lactones, lactides, glycolides, acryl containing compounds, aminotriazol, orthoesters, anhydrides, ester imides, imides, acetals, urethanes, vinyl alcohols, enolketones, and organosiloxanes.

Shell forming materials suitable for the present invention, or the resulting microdroplets, may be chemically modified for the purpose of organ/tissue targeting or quenching immunogenic activity (i.e., modification with antibodies or polyethylene glycol). The materials may also be modified by incorporation of fluorine-containing moieties. The inclusion of such moieties in the shell may make the shell less permeable to water and may alter the interaction between the shell and a fluorine-containing liquid core. Such an alteration may modify the apparent vapor pressure of the liquid core and enhance in vivo lifetime. The shell may be so modified by reacting the material with a reactive fluorine-containing compound to form a covalently bound complex.

Preferred reactive compounds for modifying proteins are either alkyl esters or acyl halides which are capable of reacting with the protein's amino groups to form an amide linkage via an acylation reaction (see ADVANCED ORGANIC CHEMISTRY pp. 417–418 (John Wiley & Sons, New York, N.Y., 4th ed., 1992)). The reactive compound is preferably added to the vaporized liquid core compound before the vapor is mixed with the protein solution prior to microdroplet formation. For example, the reactive compound can be added to the vapor phase by bubbling the vapor through a solution of the reactive compound. This solution is kept at a constant temperature which is sufficient to introduce a desired amount of reactive compound into the vapor phase. The resultant mixture, which now contains the liquid vapor and the reactive compound, is then charged to the cavitation process.

Suitable fluorine-containing alkyl esters and acyl halides are diethyl hexafluoroglutarate, diethyl tetrafluorosuccinate, ethyl heptafluorobutyrate, ethyl pentafluoropropionate, ethyl perfluorooctanoate, nonafluoropentanoyl chloride, perfluoropropionyl chloride, hexafluoroglutaryl chloride, and heptafluorobutyryl chloride.

In addition to the use of acyl halides and alkyl esters described above, it is well known to those skilled in synthetic organic chemistry that many other fluorine-containing reactive compounds can be synthesized, such as aldehydes, isocyanates, isothiocyanates, epoxides, sulfonyl halides, anhydrides, acid halides, and alkyl sulfonates, which contain perfluorocarbon moieties ($—CF_3$, $—C_2F_6$, $—C_3F_8$, $—C(CF_3)_3$). These reactive compounds can then be used to introduce fluorine moieties into any of the shell materials by choosing a combination which is appropriate to achieve covalent attachment of the fluorine moiety.

Sufficient fluorine should be introduced to decrease the permeability of the microdroplet shell to the aqueous environment, and increase the affinity of the liquid core. The shell material will preferably contain 0.5 to 20 percent by weight, and more preferably 1 to 10 percent by weight fluorine.

The microdroplets of the invention contain a liquid core of at least one biocompatible material having a boiling point above physiological temperature (i.e. 37° C.). Preferably, the liquid material should be hydrophobic. Such materials include, but are not limited to, members of the hydrocarbon, halogenated hydrocarbon, or perfluorocarbon series or mixtures thereof. The hydrophobic compound can have a linear, branched, or cyclic molecular structure. Particularly well-suited for the present invention are the perfluorocarbons, such as perfluorohexane, perfluoroheptane, perfluoroctane, perflurorononane and perflurordecalin, preferably perfluorohexane and perfluorodecalin.

The microdroplets are used in the form of a suspension in a sterile, aqueous, injectable vehicle. Such vehicles are well-known in the art. The concentration of microdroplets in the suspension will normally be in the range of $1\times10^7$ to $1\times10^{10}$, more usually $1\times10^8$ to $1\times10^9$ per ml of suspending medium and have a mean diameter of 1–10 microns, preferably 2–4 microns. Saline solution is a preferred vehicle. When in suspension, the microdroplets are monodispersed and do not coalesce. Because of their negative buoyancy, they will settle. The microdroplets may be kept in more concentrated or more dilute suspensions than specified above, and then reformulated for injection.

Microdroplets having a heat-insolubilized protein shell are made by subjecting a mixture of an aqueous solution of a heat-denaturable protein and vaporized liquid core material to mechanical cavitation, such as occurs in a colloid mill, to cause the protein to simultaneously denature and encapsulate the vaporized liquid, and cooling the mixture to below the boiling point of the liquid core material. The concentration of protein in the solution is in the range of about 0.1 to 10.% w/v, preferably about 1 to 5% w/v, and most preferably about 1% w/v. In this milling procedure, the aqueous solution of the heat-denaturable filmogenic protein is provided to the mill at a temperature necessary to achieve incipient denaturation temperature during the subsequent mechanical cavitation of the solution. The denaturation temperature of the protein in solution will normally be in the range of 50° to 100° C. It can be obtained from tables of thermal protein denaturation in the literature, or experimentally by any known method. For example, to determine the denaturation temperature experimentally, a protein solution can be heated in a water bath while stirring. The denaturation temperature is the temperature at which insoluble material is first observed. Note that the denaturation temperature is affected by the nature, purity and source of the protein, the concentration of the protein in solution, the pH, buffer, ionic strength, the presence of stabilizers and the presence of chemical denaturants or detergents. Therefore, it is necessary to determine the denaturation temperature of the protein in the environment in which it will be employed to make microdroplets. If desired, additives such as detergents or polar solvents can be employed to change the temperature at which denaturation takes place.

The following table gives the denaturation temperatures of several naturally occurring proteins which were determined experimentally as described above:

| PROTEIN | CONCENTRATION | pH | SOLVENT | $T_{desaturation}$ |
|---|---|---|---|---|
| Human Serum Albumin, USP Swiss Red Cross (Bern, Switzerland) | 50 mg/mL | 6.9 | 0.9% NaCl, 4 mM Sodium Caprylate, 4 mM Tryptophanate | 75° C. |
| Human Serum Albumin, USP Swiss Red Cross (Bern, Switzerland | 10 mg/mL | 6.9 | 0.9% NaCl, 1 mM Sodium Caprylate, 1 mM Tryptophanate | 78° C. |
| β-Lactoglobulin, Sigma (St. Louis, MO) | 25 mg/mL | 7.6 | USP Water | 90° C. |
| αβ-Globin, Sigma (St. Louis, MO) | 25 mg/mL | 5.0 | USP Water | 90° C. |
| Lysozyme Sigma (St. Louis, MO) | 100 mg/mL | 7.5 | 5 mM TRIS*, 2 mM DTT*** | 31° C. as determined immediately after addition of DTT |
| Human Gamma Globulin, acid pH method, Sigma (St. Louis, MO) | 40 mg/mL | 5.0 | 10 mM MES**, pH 5.0 | 66° C. |
| Human Gamma Globulin, alkaline pH method, Sigma (St. Louis, MO) | 40 mg/mL | 9.8 | 10 mM TRIS, pH 9.8 | 69° C. |
| apo-Transferrin, Sigma (St. Louis, MO) | 20 mg/mL | 7.5 | 10 mM TRIS* | 71° C. | vapor may be mixed with minor amounts of an inert water-soluble or water-insoluble carrier gas such as air, oxygen, nitrogen, helium, argon, $SF_6$, $CF_4$, $C_2F_6$, $C_3F_8$, or $C_4F_{10}$. When used, the carrier gas will normally constitute between about 5% v/v to 30% v/v of the vapor/carrier gas mixture.

The vapor and protein solution are combined and subjected to cavitation under conditions that produce microdroplets. This is accomplished using an apparatus in which mechanical shearing and hydrodynamic cavitation can be produced, such as high speed mixers, mills, fluidizers, and the like. A preferred apparatus is a colloid mill which is defined as "a machine consisting of a high-speed rotor and stator, dispersion or emulsification being effected by the opposing faces." ADVANCED FILTRATION AND SEPARATION TECHNOLOGY 1:108–110 (1990). Examples of specific milling apparatuses which can be used are as follows:

| | |
|---|---|
| Model #2 1/2 | Bematek, Beverly, MA |
| Model W250V | Greerco, Hudson, NH |
| Model 2F | APV Gaulin, Everett, MA |
| Model L4R | Silverson, Chesum, UK |
| Model Polytron PT3000 | Kinematica, Littaw, Switzerland |

When using a colloid mill, the rotor speed, gap size, and vapor:liquid ratio are the principle process parameters which affect the characteristics (mean size, size distribution, and concentration) of the microdroplets. Those parameters are adjusted empirically to provide a product having the desired characteristics.

After passing through the mill, the product is cooled to below the boiling point of the liquid. The population dynamics of the resulting microdroplets may be analyzed using a particle counter such as a Coulter

* TRIS=2-amino-2-(hydroxymethyl)-1,3-propanediol
** MES=2-(N-morpholino)ethanesulfonic acid
*** DTT=dithiothreitol Each apparatus employed to cavitate the protein solution/vaporized liquid mixture will introduce a certain amount of heat to the protein solution due to the mechanical shear forces exerted on the solution. That heat must be sufficient to cause localized denaturation of the protein at the liquid vapor interface. It is thus important to determine the amount of temperature increase caused by the apparatus so that the temperature at which the protein solution is introduced into the apparatus can be adjusted to achieve such local thermal denaturation. Specifically, the bulk temperature of the liquid in the apparatus must coincide with the incipient denaturation temperature immediately prior to cavitation. The cavitation event generates the additional heat necessary to locally denature the protein. Incipient denaturation temperature is defined as the temperature at which the protein is on the verge of denaturation, but the solution does not contain any denatured protein. This temperature is just below, typically 1° to 5° C. below, the denaturation temperature. If necessary, the starting protein solution may be preheated prior to being introduced into the apparatus to a temperature that allows the incipient denaturation temperature to be reached.

Once the proper starting temperature of the protein solution has been achieved, the solution is combined with the vaporized liquid, for example by introducing the vapor into the protein solution prior to or directly into the cavitation process at a volume to volume ratio in the range of about 1:20 to 2:1 vapor:liquid, preferably about 1:5 to 1:1. The proper vapor:liquid ratio will depend on the geometry of the apparatus, and can be adjusted to optimize output. The Multisizer II. Because of their specific gravity, the micro droplets will settle out of the suspension in which they are produced. They may be bottom decanted from surface foam produced in the milling process and, if necessary or desirable, resuspended in a fresh injectable vehicle and stored for use.

The microdroplet suspensions of the invention are useful as an ultrasound contrast agent to enhance the ultrasound image of body tissues or organs such as the heart, blood vessels, kidney and brain. They are particularly useful for using doppler mode to image blood flow throughout a region of interest. In each use, the suspension is injected into a peripheral vein at about 0.05 to 0.5 ml/kg body weight. Ultrasonic energy is applied to the area to be imaged and reflected energy is collected and translated into an image using conventional, commercially available ultrasound imaging equipment.

The invention is further illustrated by the following examples. These examples are not intended to limit the invention in any manner.

EXAMPLE 1

Preparation of Perfluorohexane Microdroplets with Perfluoropropane Carrier

Perfluorohexane liquid was encapsulated with human serum albumin using a 2" Gaulin colloid mill (APV Gaulin). An in-line gas-heater was used which consisted of a quartz tube (approximately 1"×10") containing a 1 KW hot filament (Glo-Quartz, Tucson, Ariz.). A 0.064" hollow stainless steel tube was coiled around the quartz tube, and the whole assembly was inserted in a 1.25" copper pipe. The ends of the copper pipe were loosely closed with glass wool. A current regulator was used to control the heating of the incandescent filament.

Perfluoropropane was used as the carrier gas, and a gas pump (Fluid Metering, Inc., Oyster Bay, N.Y.) was attached to the 0.064" tubing upstream from the in-line heater to overcome backpressure in the narrow bore tubing.

The outlet side of the in-line heater was connected to the mill feed port so that the hot gases would mix inside the mill with the liquid feed.

Liquid perflurorohexane was injected into the in-line heater just downstream of the gas pump, with a gas-tight glass syringe (Hamilton Syringe Co., Reno, Nev.). The liquid perfluorohexane was placed in the syringe and a syringe pump (Harvard Apparatus Co.) was used. This set-up allowed the liquid to be mingled with the carrier gas and thus vaporized prior to entry in the mill.

A thermocouple was inserted into the gas line just before the mill to measure temperature of the vapor mixture.

The following parameters were used:

Perfluoropropane gas feed 30 ml/min.
Perfluorohexane liquid feed 1.1 ml/min.
Vapor temperature 130° C.
1% Albumin feed 300 ml/min.
Process temperature 76° C.

Microscopy of the milled product revealed a population of negatively buoyant, irregularly shaped microdroplets. Echogenicity was observed to be 4 hours or greater in a circulating in vitro phantom. This can be compared to average echogenicity durations of 30 minutes for microspheres comprising albumin encapsulated perfluorocarbon gas and to a matter of minutes for microspheres comprising albumin encapsulated air.

EXAMPLE 2

Preparation of Perfluorohexane Microdroplets with Air Carrier

All parameters were identical to those in Example 1, with the exception that air was used as the carrier and was supplied at a rate of 40 ml/min. The resulting microdroplets did not differ in appearance from those produced in Example 1.

EXAMPLE 3

Preparation of Perfluorodecalin with Perfluoropropane Carrier

The set-up was identical to that used in Example 1, with the following parameters employed:

Perfluoropropane gas feed 25 ml/min.
Perfluorodecalin liquid feed 5 ml/min.
Vapor temperature 150° C.
1% Albumin feed 300 ml/min.
Process temperature 77° C.

The resulting microdroplets did not differ in appearance from those produced in Example 1.

Modifications of the above-described modes for carrying out the invention that are obvious to those of skill in the ultrasound contrast agent art are intended to be within the scope of the following claims.

We claim:

1. A composition for use as an ultrasonic imaging agent comprising a suspension of negatively buoyant aspherical microdroplets, said microdroplets comprising:

(a) an inner core of at least one biocompatible liquid, said core encapsulated by (b) a shell made from an amphiphilic biocompatible material.

2. The composition of claim 1 wherein said shell material is a heat-insolubilized filmogenic protein.

3. The composition of claim 2 wherein said shell material is human serum albumin.

4. The composition of claim 2 wherein said microdroplets have a mean nominal diameter in the range of 1–10 microns.

5. The composition of claim 2 wherein the concentration of the microdroplets in the suspension is in the range of $1 \times 10^7$ to $1 \times 10^9$ microdroplets per ml of suspension.

6. The composition of claim 1 wherein the liquid is selected from the group consisting of hydrocarbons, halogenated hydrocarbons, perfluorocarbons, or mixtures thereof.

7. The composition of claim 1 wherein the shell material is human serum albumin and the liquid is perfluorohexane.

8. The composition of claim 1 wherein the shell material is human serum albumin and the liquid is perfluoroheptane.

9. The composition of claim 1 wherein the shell material is human serum albumin and the liquid is perfluorooctane.

10. The composition of claim 1 wherein the shell material is human serum albumin and the liquid is perfluorononane.

11. The composition of claim 1 wherein the shell material is human serum albumin and the liquid is perfluorodecalin.

12. The composition of claim 1 wherein the shell is modified to include moieties that target a specific tissue or organ.

13. A method of enhancing the contrast of tissue and/or organs of a patient in an ultrasonic image thereof comprising:
    (a) injecting the composition of claim 1 into the patient;
    (b) applying ultrasonic energy to said tissue and/or organs;
    (c) detecting ultrasonic energy that is reflected from the tissues and/or organs; and
    (d) translating the reflected energy into an image.

14. The method of claim 13 wherein the imaging is performed in doppler mode.

15. A method of making an ultrasonic imaging agent comprising:
    (a) subjecting a mixture of:
        (i) an aqueous solution of a heat-insolubilized filmogenic protein, and
        (ii) a vaporized biocompatible liquid to mechanical cavitation under conditions that heat insolubilizes the protein; and
    (b) cooling the mixture to a temperature below the boiling point of the liquid, whereby a suspension of aspherical microdroplets comprising a liquid core encapsulated by a shell of heat-insolubilized filmogenic protein is prepared.

16. The method of claim 15 wherein the protein is human serum albumin and its concentration in solution is in the range of 1 to 5% by weight, inclusive.

17. The method of claim 15 wherein the vaporized liquid is mixed with a carrier gas.

18. The method of claim 15 wherein the vaporized liquid is selected from the group consisting of perfluorohexane, perfluoroheptane, perfluorooctane, perfluorononane and perfluorodecalin, and the gas carrier is selected from the group consisting of air, oxygen, argon, nitrogen, helium, perfluoromethane, perfluoroethane, perfluoropropane, perfluorobutane, and $SF_6$.

19. The method of claim 15 wherein the mechanical cavitation is carried out in a colloid mill.

* * * * *